United States Patent [19]
Phelps

[11] Patent Number: 5,207,647
[45] Date of Patent: May 4, 1993

[54] NEEDLE DEVICE

[76] Inventor: David Y. Phelps, 640 Worcester Rd. #204, Framingham, Mass. 01701

[21] Appl. No.: 788,253

[22] Filed: Nov. 5, 1991

[51] Int. Cl.⁵ ............................................. A61M 5/00
[52] U.S. Cl. .................................... 604/158; 604/164
[58] Field of Search ............... 604/157, 158, 164, 165, 604/274, 161

[56] References Cited

U.S. PATENT DOCUMENTS

| | | | |
|---|---|---|---|
| 3,727,613 | 4/1973 | Sorenson et al. | 604/165 |
| 4,399,023 | 9/1982 | Gross | 604/169 |
| 4,654,030 | 3/1987 | Moll et al. | 604/165 |
| 4,772,264 | 9/1988 | Cragg | 604/165 |
| 4,865,593 | 9/1989 | Ogawa et al. | 604/160 |
| 4,898,000 | 12/1989 | McQuilken et al. | 604/160 |
| 4,940,458 | 7/1990 | Cohn | 604/158 |
| 4,969,875 | 11/1990 | Ichikawa | 604/164 |
| 4,994,036 | 2/1991 | Biscoping et al. | 604/158 |
| 5,104,382 | 4/1992 | Brinkerhoff et al. | 604/165 |
| 5,106,376 | 4/1992 | Mononen et al. | 604/164 |
| 5,116,353 | 5/1992 | Green | 604/164 |

Primary Examiner—Paul J. Hirsch

[57] ABSTRACT

A needle device for delivering medicaments to the body of a patient, the device including an elongated housing having a catheter on one end, with a trocar arranged through the end of the housing and the catheter. The trocar is reciprocably advancable and retractable with respect to the catheter. A spring biased carriage in the housing controls the movement of the trocar and causes it to retract from the distal end of the catheter after the catheter and trocar have been advanced into a body and the trocar no longer encounters resistance to forward or distally directed advance of the device.

26 Claims, 5 Drawing Sheets

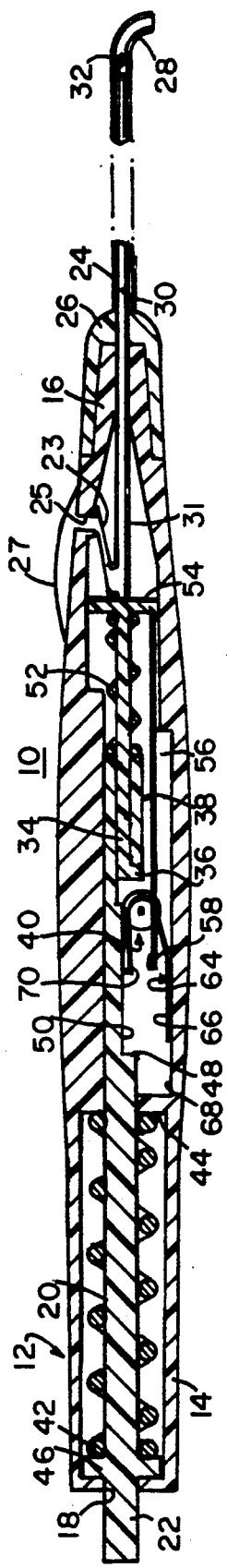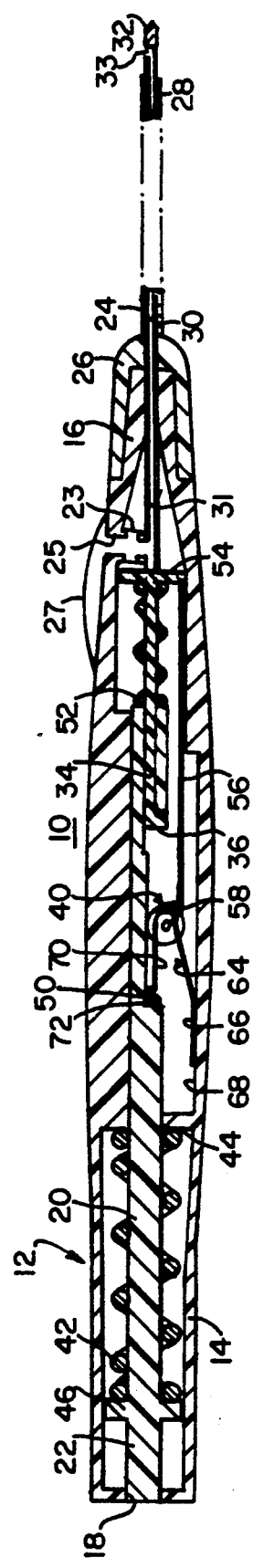

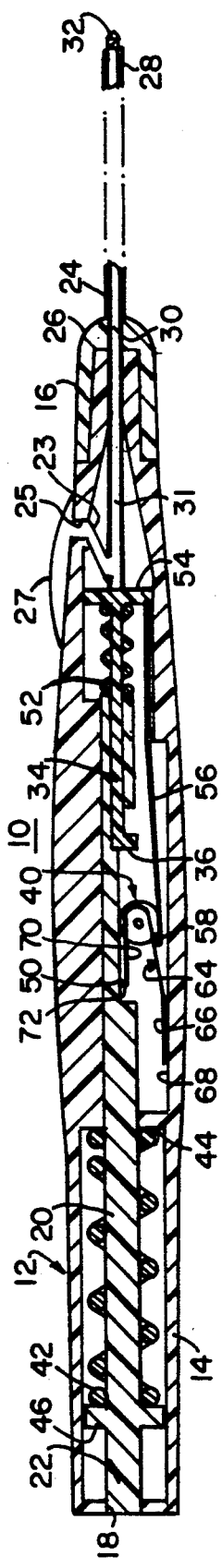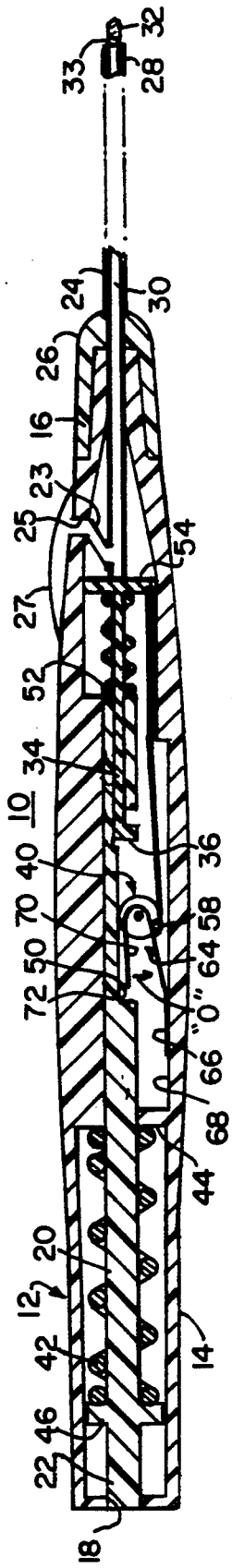
FIG.3
FIG.4

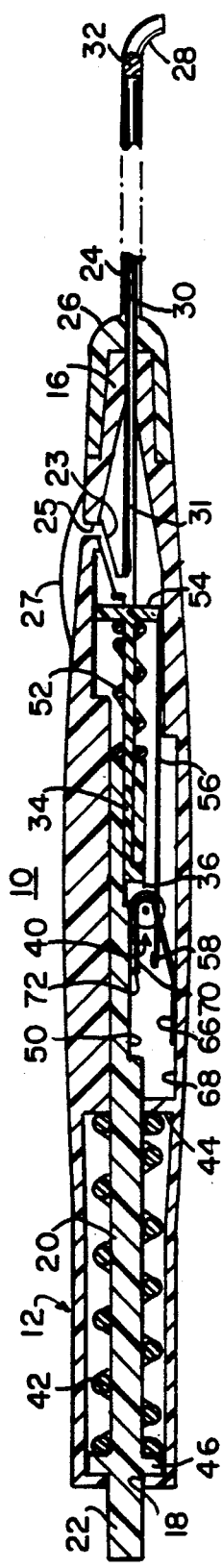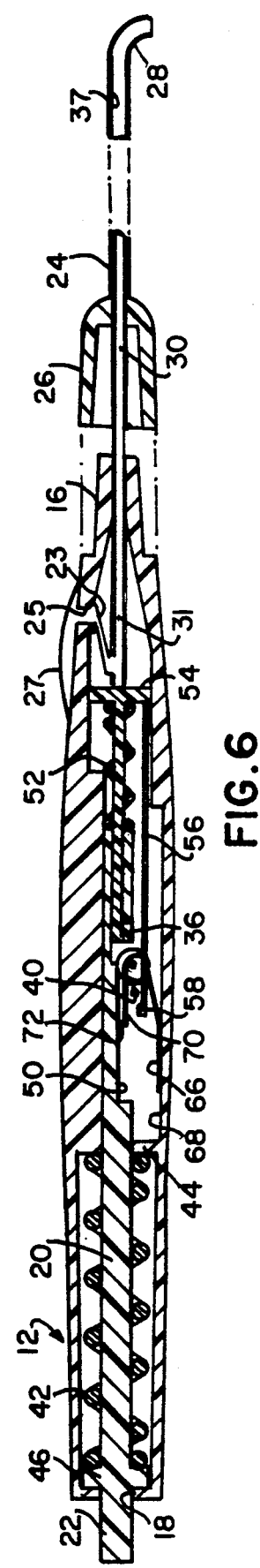
FIG.5
FIG.6

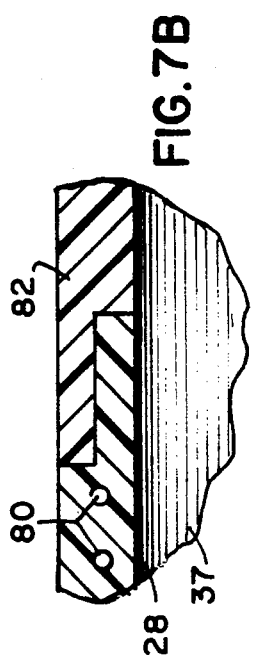
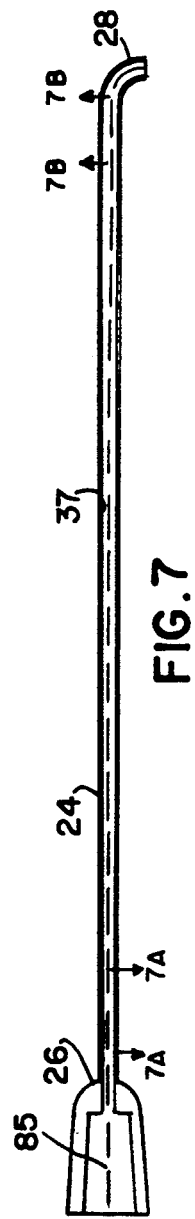
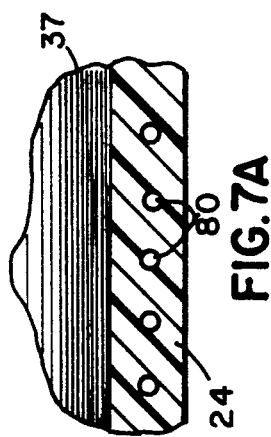
FIG. 7B
FIG. 7
FIG. 7A

NEEDLE DEVICE

BACKGROUND OF THE INVENTION

(1) Field of the Invention

This invention relates to epidural needle devices, and more particularly to medical devices for introducing a needle and/or catheter into the epidural space of a patient.

(2) Prior Art

Epidural anesthesia is a common medical procedure utilized to deliver drugs or local anesthetics to a patient undergoing a major surgical procedure, obstetrical delivery, or diagnostic/theraputic nerve block. There are several methods of doing this. The most common is the loss-of-resistance technique where a needle with a syringe containing saline and /or air is advanced into the patient's epidural space, which is adjacent to the dural sack. As the needle is advanced, the plunger of the syringe is tapped to give a gentle increase in pressure. Resistance to advancement of the plunger in the syringe is felt by the physician as the needle is advanced through the patient's tissues toward the ligamentum flavum. As the needle passes through the ligamentum flavum and enters the epidural space, a sudden loss of resistance to advancement of the plunger will occur. The saline and air can then be injected with ease into the epidural space as a test, thus indicating the proper location of the needle tip. The advancement of the needle should cease once the epidural space has been entered. Otherwise, the needle may pierce the dural sack.

This loss-of-resistance technique is done in 1-2 mm. advances where the syringe plunger is tapped to check for the loss of resistance. The entry into the epidural space is confirmed by the absence of plunger pressure resistance. The syringe would then be separated from the needle for the "single shot" injection of drugs, or the insertion of a catheter into the epidural space, after which the needle is removed. The catheter insertion permits a continuous infusion of medicaments into the epidural space.

A catheter set for spinal anesthesia is shown in U.S. Pat. No. 4,994,036 to Biscoping et al., which includes the use of a guidewire fed into the epidural space, which fits through the needle device after it has been advanced into the epidural space by the loss-of resistance technique.

A trocar assembly is shown in U.S. Pat. No. 4,654,030 to Moll et al, utilized for puncturing a body cavity for subsequent drainage by a cannula. This assembly utilizes a spring loaded safety shield with a fixed trocar, with no visual or audible indicator arrangement.

BRIEF SUMMARY OF THE INVENTION

The present invention provides an epidural needle device which, when cocked, permits penetration of its distal tip into a body until it senses a space or void. The tip, which is a trocar, is then retracted automatically within the device, preventing further cutting capabilities of that trocar.

The present invention comprises an epidural needle device having an elongated housing. The housing has a proximal and a distal end. An opening is arranged through the proximalmost end of the housing. A carriage shaft is disposed within the housing and extends slightly outwardly of the proximal opening.

An elongated catheter is attached to the distal end of the housing through a hub. The distalmost end of the catheter comprises a pre-curved tip thereon. A needle or trocar is slidably disposed through the catheter. The distal end of the needle or trocar has a pointed tissue piercing tip. The proximal end of the needle or trocar is engaged with a detent assembly arranged at the distal end of the carriage shaft.

A first compressive spring is arranged within the housing to provide a proximally directed bias onto the carriage shaft. A second compressive spring is arranged within the housing, about the proximal end of the trocar, but which spring has less force than the first spring. The distal end of the second spring keeps a forwardly or distally directed bias upon a flange on the trocar. The proximal end of the second spring engages the distal end of the carriage shaft. The flange on the trocar has a proximally extending finger or link which engages the detent assembly. The link rotates the detent assembly to effectuate rearward retraction of the carriage shaft and the trocar with respect to the housing.

In operation of the present invention, the epidural needle device is initially cocked by the attending physician, by pressing upon the proximalmost end of the carriage shaft. This causes the detent assembly to become engaged with the carriage shaft, and compresses the first spring. The trocar is also caused to extend outwardly slightly beyond the distal end of the catheter shaft, causing the exposure of the cutting tip of the trocar and straightening of the precurved catheter.

Penetration of skin, tissue and ligaments by gentle force applied to the device into a patient, causes a slight rearward pressure and movement on the trocar, simultaneously compressing the second spring and causing the link to move to a position that upon any forward motion of the needle link assembly, the link will rotate the detent assembly and thus release the carriage.

Upon entry of the trocar into the epidural space, the trocar is advanced distally very slightly by bias of the second spring thereagainst. This slight forward or distal advance of the trocar causes the link attached to it to trip the detent assembly, thus releasing the carriage shaft from capture, whereupon the first, more powerful spring pushes the carriage shaft and attendently attached trocar rearwardly or proximally, with an audible sound. This causes the trocar to also be retracted proximally which allows the elongated catheter to return to its right angle bend. The proximal end of carriage shaft is also caused to extend out through the opening in the proximal end of the housing, to provide a visual indication of penetration into the epidural space, as well as the audible indication of such entry.

It is apparent that this device may also be used to locate/enter other spaces or potential spaces in the body where there is less resistance than in the surrounding tissue.

BRIEF DESCRIPTION OF THE DRAWINGS

The objects and advantages of the present invention will become more apparent when viewed in conjunction with the following drawings, in which:

FIG. 1 is a side elevational view insection of an epidural needle device in a "packaged" configuration;

FIG. 2 is a view similar to FIG. 1, showing the epidural needle device in its "cocked" configuration;

FIG. 3 is a view similar to FIG. 1, showing the epidural needle device during penetration of tissue;

FIG. 4 is a view similar to FIG. 1, showing the epidural needle device just as it enters the epidural space;

FIG. 5 is a view similar to FIG. 1, showing the epidural needle device after it has entered the epidural space;

FIG. 6 is a view of the needle device being removed from its catheter tip;

FIG. 7 is a side view of the catheter with portions such as sub-figures 7A and 7B being enlarged for clarity of showing.

DESCRIPTION OF THE PREFERRED EMBODIMENT

Figure 8:
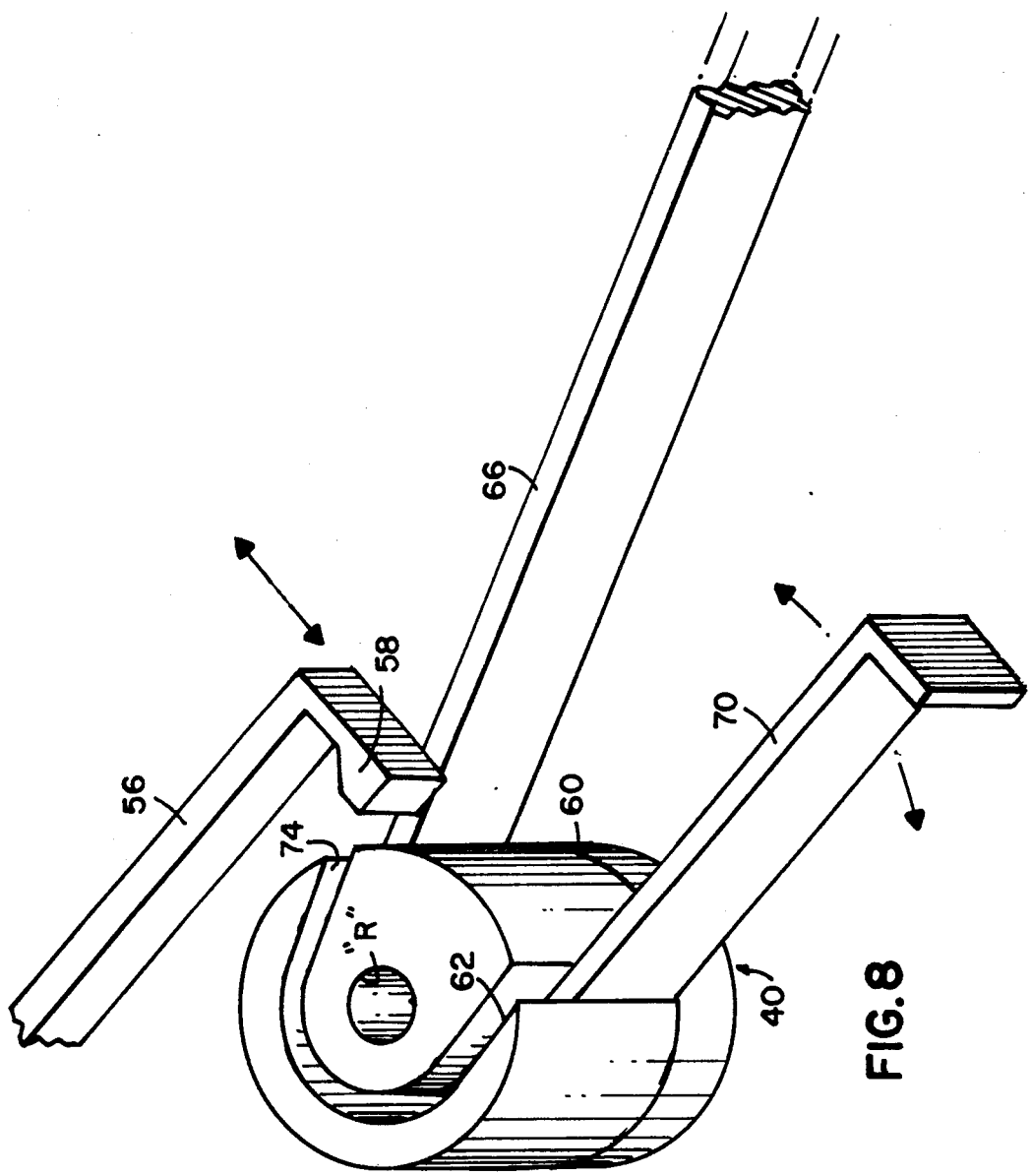
FIG. 8 is a perspective view of a detent assembly which would otherwise be arranged within the epidural needle device.

Referring now to the drawings in detail, and particularly to FIG. 1, there is shown an epidural needle device 10, having an elongated housing 12 having a proximal end 14 and a distal end 16. A proximal opening 18 is arranged through the proximal end 14 of the housing 12. A longitudinally slidable carriage shaft 20 is disposed within the housing 12, and has a proximal end 22 which extends slightly outwardly of the proximal opening 18, when the epidural needle device is shown in its "packaged" or "shipping" configuration depicted in FIG. 1.

An elongated catheter 24 is attached to the distal end 16 of the housing 12 through a mating hub 26. The catheter 24 has a pre-curved tip 28 on its distalmost end, to configure the lumen therein about 90 degrees from the longitudinal axis of the body of the catheter 24. A tubular needle comprising the distal end of a trocar assembly 30 is slidably disposed within the lumen of the catheter 24. The needle or trocar 30 has a pointed tissue piercing tip 32 on its distalmost end. A discharge opening 33 is disposed proximally adjacent the tip 32, the opening 33 being in fluid communication with a lumen 31 in the tubular trocar 30. A resilient bulb 27 is arranged on the distal end 16 of the housing 12. An opening 25 is arranged through the sidewall of the housing 12 radially inwardly of the bulb 27. The opening 25 is in fluid communication with the lumen 31 at the proximal end of the trocar 30 through a flexible tubular conduit 23 arranged therebetween, as shown in the drawings in various degrees of stretch.

The trocar assembly 30 has a proximal end 34 which extends into the distal end 16 of the housing 12 and has an extended lip 36 which slidably engages a flange 38 on the distal end of the carriage spring 20, which is adapted to facilitate engagement and disengagement of a detent assembly 40, shown more clearly in FIG. 8.

A first compressive spring 42 is arranged within the housing 12 between an abutment 44 therein disposed about the carriage shaft 20 and an annular flange 46 secured to the carriage shaft 20 near its proximal end 22. The first compressive spring 42 provides a rearward or proximally directed bias onto the carriage shaft 20.

A stepped shoulder 48 is arranged about the midpoint of the carriage shaft 20, as shown in FIG. 1. A notch 50 is disposed transversely across the carriage shaft 20 adjacent the shoulder 48.

A second compressive spring 52 is disposed about a portion of the proximal end 34 of the trocar 30. The second spring 52 has a distal end which abuts an annular flange 54 which is disposed about the approximate midpoint of the trocar assembly 30. The second spring 52 has a proximal end which is in abutting engagement with the distalmost end of the carriage shaft 20 and the flange 38 thereon. An elongated resilient finger or link 56 is attached to the flange 54 and extends rearwardly therefrom. The link 56 has a "J" shaped distalmost tip 58 which engages the detent assembly 40.

The detent assembly 40, shown more explicitly in FIG. 8, comprises a pivot hub 60 which is pivotably secured to an inside wall of the housing 12. The pivot hub 60 is of generally cylindrical configuration and has a "U"-shaped notch 62 molded thereacross, around its axis of rotation "R". An elongated "U"-shaped spring 64 is disposed within the notch 62, as shown in FIGS. 1-5 and shown most clearly in FIG. 8. The U-shaped spring 64 has a first leg 66 that presses against a wall 68 on the inside of the housing 12. The U-shaped spring 64 has a second leg 70 having a flange 72 on its distalmost end. The flange 72 is sized so as to readily engage and disengage the transversely disposed notch 50 adjacent the shoulder 48 of the carriage shaft 20.

The pivot hub 60 has sufficient axial length to allow the notch 62 to have an engagement lip 74 adjacent one end of the U-shaped notch 62, as shown in FIG. 8, immediately adjacent the leg 66 of the spring 64.

The distalmost tip 58 of the link 56 is arranged to mate with the engagement lip 74 and give it a slight "pull" to cause it to rotate (counter clockwise as shown in the drawings) so as to lift the flange 72 from the notch 50 in the carriage shaft 20, as will be explained hereinbelow.

The catheter 24 shown by itself in FIG. 7 may have a braid reinforcement 80 woven within its walls, as shown in the enlarged view in FIG. 7A. The catheter 24 alternatively, may have a pair of partial slits 85 extending longitudinally along its entire length, so as to permit the catheter 24 to be peeled apart, from its hub 26 to its tip 28 to facilitate removal thereof from a patient. The proximalmost end half of the distal tip 28 is made of a flexible plastic material 82 without the reinforcement 80, as shown in FIG. 7B, permitting it to flex to its pre-curved configuration upon retraction of the trocar therefrom.

In operation of the epidural needle device 10 the attending physician "cocks" it from its "packed" state shown in FIG. 1 to its "cocked" state by pressing the proximal end 22 of the carriage shaft 20 distally, or to the right, as shown in FIG. 2, thereby compressing the first spring 42 and the less strong second spring 52 as well as bringing the notch 50 into mating engagement with the flange 72 of the outwardly biased U-shaped spring 64. The tip 32 of the trocar assembly 30 is also at this time, once the device 10 has been cocked, to be caused to extend about 2 mm. beyond the distalmost end of the catheter tip 28, straightening out the pre-curved catheter tip 28 and simultaneously permitting the cutting portion of the trocar assembly 30 to be distally exposed.

Gentle but constant pushing force by the physician on the epidural needle device 10 penetrates the patient's skin, soft tissue and ligaments, and causes the trocar assembly 30 including the link 56, to be pushed-back into the catheter 24 slightly, (to the left) as shown in FIG. 3, and also compressing the second compressive spring 52 slightly, and moving the tip 58 of the link 56 proximally past the pivot hub 60.

Upon entering the epidural space, the trocar assembly 30 encounters less resistance, and is therefore caused to advance slightly, for this example about 0.25 mm. because of its forward (distally directed) bias from the second compressive spring 52 acting upon the annular flange 54 secured thereto, the trocar assembly 30 being shown thusly in FIG. 4. The distal tip 58 of the link 56 mates with the lip 74 on the hub 60.

As the trocar assembly 30 advances for example, about 0.25 mm. upon meeting with sudden diminished resistance upon entering the epidural space it also causes the link 56 to advance forwardly a corresponding amount. The frontwardly moving (distal) end 58 of the link 56 having been engaged with the engagement lip 74 of the pivot hub 60, causes the pivot hub 60 to rotate slightly, about its axis of rotation "R", counter clockwise as shown in the drawings, to cause the rotation of the second leg 70 of the U-shaped spring 64 counter clockwise as well, lifting the flange 72 out from locking engagement in the notch 50 of the carriage shaft 20, as indicated by the arrow "O" in FIG. 4.

The first compressive spring 42, being stronger than the second compressive spring 52 is thus released, so as to push the carriage shaft 20 rearwardly, or theleft, as shown in FIG. 4, by an arrow "L", this occurring with an audible click, as the flange 46 hits the proximal wall of the housing 12, the spring 42, as shown in FIG. 5, by the pushing of the proximal end 22 of the carriage shaft 20 out of the proximal opening 18 in the housing 12. During the rearward travel of the carriage shaft 20, the trocar assembly 30 to which the carriage shaft 20 is engaged, is also pulled proximally (rearwardly) by the first compressive spring 42, as depicted in FIG. 5.

A "loss of resistance" test may be undertaken during this procedure, by the pressing of the resilient bulb 27 to determine if the opening 33 in the distal end of the trocar assembly 30 has yet encountered a void or body cavity. Upon the encountering of the void or epidural space, the trocar assembly 30 no longer feels the resistance to its advance and retracts as aforementioned. Upon the retraction of the trocar assembly 30 and particulatly the tip 32 of from the distal pre-curved tip 28 of the catheter 24, the tip 28, being pre-curved, is permitted to assume its bent configuration, as shown in FIG. 5.

FIG. 6 shows the housing 12 and its enclosed/attached trocar assembly 30 being removed from the catheter 24, to facilitate delivery of medicaments (or other catheters or medical devices) through the catheter 24 after the distal end of the trocar assembly 30 has been removed therefrom. Additionally, the catheter 24 itself, with its pre-curved tip 28 could also be directed further into the bodt duct.

Thus, what has been shown and described is a unique needle device suitable particularly for epidural procedures, which permits single handed advance into body tissue, and when the trocar upon entering an epidural space and sensing no resistance to further forward advance, minutely advances on its own, well within distance limitations of the epidural space, only to trigger its own immediate retraction, removing the cutting and piercing component from exposure, presenting to that epidural space a soft pre-curved catheter tip for subsequent adaptation to a medicament supply source upon removal of the trocar and drive assembly from the catheter shaft.

I claim:

1. A needle device for the delivery of medicaments, comprising:
    an elongated housing;
    a reciprocable hollow needle having a proximal end and a distal end with a lumen there between, said proximal end secured within said housing;
    a catheter disposed about said hollow needle, said catheter having a distal end and a proximal end, said proximal end of said catheter being attached to said housing;
    an arrangement of compressable and releasable springs disposed within said housing and attached to said hollow needle so as to bias said hollow needle therefrom; and
    a detent assembly to actuate retraction of said hollow needle within said catheter upon a decrease in pressure upon said hollow needle as it is being advanced into a space or potential space.

2. A needle device for the delivery of medicaments, as recited in claim 1, wherein said arrangement of springs includes a first compressive spring and a carriage shaft for reaction with said first compressive spring, and a second compressive spring, interacting so as to effectuate retraction of said hollow needle.

3. A needle device for the delivery of medicaments, catheters or medical devices, comprising:
    an elongated housing having a proximal end and a distal end;
    a hollow needle movably arranged through the distal end of said housing;
    a catheter attached to the distal end of said housing, said hollow needle movably arranged through said catheter and adapted to be distally co-terminous therewith; and
    means for effectuating retraction of said hollow needle from a distally co-terminous relationship with said catheter upon the engaging of a void in a body by said distal end of said catheter and said hollow needle.

4. A needle device for delivery of an medicaments, comprising:
    an elongated housing having a proximal end and a distal end;
    a catheter having a lumen and a needle having a lumen, said needle with said lumen co-extensively arranged within the lumen of said catheter on the distal end of said housing;
    a means for retracting said needle into said housing and with respect to said catheter; and
    an indicator means on the proximal end of said housing to visually signal the retraction of said needle with said lumen with respect to said catheter and said housing, to indicate the sensing of a void in a body into which said device has been advanced.

5. A needle device for delivery of medicaments, as recited in claim 4, wherein said distal tip of said catheter is pre-curved so as to permit its automatic curvature thereof when said needle with said lumen is retracted therefrom.

6. A needle device for delivery of medicaments, as recited in claim 4, wherein said means for retracting said needle with said lumen into said housing comprises a pair of springs in combination with a detent assembly to pull said needle with said lumen at least partway into said housing.

7. A needle device for delivery of medicaments, as recited in claim 4, wherein said catheter has a distal end and a proximal end, said distal end being made of softer more flexible construction than said proximal end.

8. A needle device for delivery of medicaments, as recited in claim 7, wherein said proximal end of said catheter has a braided reinforcement woven into its walls.

9. A needle device for the delivery of medicaments as recited in claim 4, including a means for testing for the loss of resistance to fluid backpressure within the lumen of said needle with said lumen.

10. A needle device for the deliver of medicaments, as recited in claim 7, wherein said distal end of said catheter has a pre-curve arranged therein.

11. A needle device for the delivery of medicaments, as recited in claim 9, wherein said means for testing for loss of resistance comprises a resilient bulb disposed adjacent the distal end of said elongated housing, said resilient bulb defining a chamber which is in fluid communication with the distal end of said needle with said lumen.

12. A needle device for the delivery of medicaments, comprising:
 an elongated housing having a proximal end and a distal end;
 a reciprocable hollow needle having a proximal end and a distal end, said proximal end of said hollow needle securable to a carriage shaft within said housing;
 a catheter having a proximal end and a distal end, said proximal end attachable to said distal end of said housing and over said reciprocably movable hollow needle;
 said carriage shaft biasedly arranged within said housing and attached at one end to the proximal end of said housing;
 a spring adapted to bias said hollow needle distally; and
 a detent assembly engagable with said carriage shaft to permit said hollow needle and carriage shaft to be biased proximally by a second spring arrangement.

13. A needle device for the delivery of medicaments, as recited in claim 12, wherein said carriage shaft has a proximal end which extends out of the proximal end of said housing when said hollow needle is biased proximally.

14. A needle device for the delivery of medicaments, as recited in claim 13, wherein the distal end of said catheter shaft automatically forms a curve therewithin when said hollow needle is biased proximally within said housing.

15. A needle device for the delivery of medicaments, as recited in claim 14, wherein the proximal end of said catheter is disengagable from said housing and said proximally biased hollow needle.

16. A needle device for the delivery of medicaments, as recited in claim 15, wherein the proximal end of said catheter has a brain reinforcement arranged therewithin.

17. A method of delivering medicaments to a body comprising the steps of:
 advancing into a body space a needle device having an elongated housing with a hollow needle at a distal end thereof, said hollow needle arranged within a catheter, said hollow needle having a proximal end biased distally by a spring arrangement within said housing;
 puncturing a body space by said hollow needle which extends distally beyond the distal end of said catheter; and
 retracting said hollow needle proximally upon said hollow needle losing resistance to forward or distal advance in a body.

18. A method of delivering medicaments to a body as recited in claim 17, including the steps of:
 exposing a visual indicator from the proximal end of said housing upon said retraction of said hollow needle proximally with respect to said catheter; and
 curving the distal end of said catheter upon retraction of the hollow needle therefrom.

19. A method of delivering medicaments to a body as recited in claim 18, including the step of:
 testing the entry of said hollow needle into a void in a body organ by applying compressive pressure to a flexible bulb which defines a chamber which is in fluid communication with the distal tip of said hollow needle.

20. A method of delivering medicaments to a body as recited in claim 19, including the step of:
 withdrawing said hollow needle and said elongated housing from said catheter so as to permit said catheter to be adapted to a medicament supply.

21. A method of delivering medicaments to a body as recited in claim 19, including the step of:
 withdrawing said hollow needle and said elongated housing from said catheter;
 inserting a further medical instrument into said body through said now empty catheter engaged within the body.

22. A method of delivering medicaments to a body as recited in claim 19, including the step of:
 withdrawing said hollow needle only partway from the distal end of said catheter so as to maintain pushability of said catheter in said hollow needle portion thereof to allow the distal pre-curved portion of said catheter to be pushed further into the body.

23. A reciprocable actuable needle device for the delivery of medicaments to a body, comprising:
 a longitudinally splitable catheter removable attached to the distal end of an elongated housing, said housing having a proximal end as well as a distal end;
 a hollow needle assembly arranged within both said housing and said catheter;
 means for biasing said hollow needle assembly proximally upon loss of resistance against said hollow needle assembly during movement of said needle device in a body; and
 indicator means to alert a needle device user that said hollow needle has no further resistance to further distally directed movement in a body.

24. A reciprocable actuable needle device as recited in claim 23, wherein said indicator means is a visual indicator.

25. A recprocable actuable needle device as recited in claim 23, wherein said indicator means is an audible indicator.

26. A reciprocable actuable needle device as recited in claim 23, including a flexible means on said distal end of said catheter which is bendable in response to retraction of said hollow needle therefrom.

* * * * *